US00PP17965P2

(12) United States Plant Patent
Miedema-Jorna

(10) Patent No.: US PP17,965 P2
(45) Date of Patent: Aug. 28, 2007

(54) **NEW GUINEA *IMPATIENS* PLANT NAMED 'TAMAR SCARLET RED'**

(50) Latin Name: *Impatiens hawkeri*
Varietal Denomination: Tamar Scarlet Red

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/358,887

(22) Filed: Feb. 17, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of New Guinea *Impatiens* plant named 'Tamar Scarlet Red', characterized by its upright, outwardly spreading and uniformly mounded plant growth habit; freely branching and freely flowering habit; dark green-colored foliage; and large rounded bright red-colored flowers.

2 Drawing Sheets

Botanical designation: *Impatiens hawkeri.*
Cultivar denomination: 'Tamar Scarlet Red'.

BACKGROUND OF THE INVENTION

The present Invention relates to a new and distinct cultivar of New Guinea *Impatiens* plant, botanically known as *Impatiens hawkeri,* and hereinafter referred to by the name 'Tamar Scarlet Red'.

The new *Impatiens* is a product of a planned breeding program conducted by the Inventor in De Lier, The Netherlands. The objective of the breeding program is to develop new *Impatiens* cultivars with large rounded flowers and attractive foliage and flower coloration.

The new *Impatiens* originated from a cross-pollination made by the Inventor in 2002 with the *Impatiens hawkeri* cultivar Tamar Cherry Red, disclosed in U.S. Plant Pat. No. 15,646, as the female, or seed, parent with the *Impatiens hawkeri* cultivar Kitamb, disclosed in U.S. Plant Pat. No. 14,047, as the male, or pollen, parent. The cultivar Tamar Scarlet Red was discovered and selected by the Inventor as a flowering plant within the progeny of the stated cross-pollination in a controlled environment in De Lier, The Netherlands.

Asexual reproduction of the new cultivar by terminal cuttings in De Lier, The Netherlands since 2002, has shown that the unique features of this new *Impatiens* are stable and reproduced true to type in successive generations.

SUMMARY OF THE INVENTION

The following traits have been repeatedly observed and are determined to be the unique characteristics of 'Tamar Scarlet Red'. These characteristics in combination distinguish 'Tamar Scarlet Red' as a new and distinct *Impatiens* cultivar:

1. Upright, outwardly spreading and uniformly mounded plant growth habit.
2. Freely branching and freely flowering habit.
3. Dark green-colored foliage.
4. Large rounded bright red-colored flowers.

Plants of the new *Impatiens* can be compared to plants of the female parent, the cultivar Tamar Cherry Red. In side-by-side comparisons conducted in De Lier, The Netherlands, plants of the new *Impatiens* differed from plants of the cultivar Tamar Cherry Red in the following characteristics:

1. Plants of the new *Impatiens* had larger flowers than plants of the cultivar Tamar Cherry Red.
2. Plants of the new *Impatiens* and the cultivar Tamar Cherry Red differed in flower color.

Plants of the new *Impatiens* can be compared to plants of the male parent, the cultivar Kitamb. In side-by-side comparisons conducted in De Lier, The Netherlands, plants of the new *Impatiens* differed from plants of the cultivar Kitamb in the following characteristics:

1. Plants of the new *Impatiens* were more compact than plants of the cultivar Kitamb.
2. Plants of the new *Impatiens* flowered earlier than plants of the cultivar Kitamb.

Plants of the new *Impatiens* can also be compared to plants of the cultivar Tamar Red, not patented. In side-by-side comparisons conducted in De Lier, The Netherlands, plants of the new *Impatiens* differed from plants of the cultivar Tamar Red in the following characteristics:

1. Plants of the new *Impatiens* flowered later than plants of the cultivar Tamar Red.
2. Plants of the new *Impatiens* had larger flowers than plants of the cultivar Tamar Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens.*

The photograph on the first sheet comprises a side perspective view of a typical flowering plant of 'Tamar Scarlet Red' grown in a container.

The photograph on the second sheet is a close-up view of typical flowers of 'Tamar Scarlet Red'.

DETAILED BOTANICAL DESCRIPTION

Plants of the cultivar Tamar Scarlet Red have not been observed under all possible environmental conditions. The phenotype may vary somewhat with variations in environment such as temperature and light intensity, without, however, any variance in genotype.

The aforementioned photographs, following observations and measurements describe plants grown in De Lier, The Netherlands, under commercial production practice in a glass-covered greenhouse during the summer. Rooted young plants were planted in 12-cm containers and the aforementioned photographs and following observations and measurements were taken about ten weeks later. During the production of the plants, day and night temperatures averaged 20° C. In the following description, color references are made to The Royal Horticultural Society Colour Chart, 1995 Edition, except where general terms of ordinary dictionary significance are used.

Botanical classification: *Impatiens hawkeri* cultivar Tamar Scarlet Red.

Parentage:

*Female parent.*—*Impatiens hawkeri* cultivar Tamar Cherry Red, not patented.

*Male parent.*—*Impatiens hawkeri* cultivar Kitamb, not patented.

Propagation:

*Type cutting.*—Terminal tip cuttings.

*Time to initiate roots, summer.*—About 5 to 7 days at 19 to 20° C.

*Time to initiate roots, winter.*—About 6 to 8 days at 19 to 20° C.

*Time to produce a rooted young plant, summer.*—About 14 to 19 days at 19 to 20° C.

*Time to produce a rooted young plant, winter.*—About 14 to 21 days at 19 to 20° C.

*Root description.*—Fine; white to brown in color.

Plant description:

*General appearance.*—Upright, outwardly spreading and uniformly mounded plant growth habit; freely branching habit; bushy appearance; freely flowering. Moderately vigorous.

*Crop time.*—From a rooted cutting, about nine weeks are required to produce finished flowering plants in 12-cm containers.

*Plant height.*—About 19 cm.

*Plant diameter or spread.*—About 39 cm.

*Lateral branches.*—Quantity per plant: About nine. Length: About 15 cm. Diameter: About 8 mm. Internode length: About 4 cm. Strength: Moderate. Texture: Smooth, glabrous. Luster: Slightly glossy. Color: 183A tinted with 146A to 146B.

*Foliage description.*—Arrangement: Primarily in whorls with about five leaves per whorl; simple. Length: About 11.5 cm. Width: About 4.4 cm. Shape: Elliptic. Apex: Acute. Base: Attenuate. Margin: Serrulate with ciliation. Texture, upper and lower surfaces: Smooth, glabrous. Luster, upper and lower surfaces: Moderately glossy. Venation pattern: Pinnate. Color: Developing foliage, upper surface: 144A. Developing foliage, lower surface: 147C. Fully expanded foliage, upper surface: Between 139A and darker than 147A; venation, 194B to 194C. Fully expanded foliage, lower surface: 191A; towards the base, 147C; venation, 182C. Petiole: Length: About 4 cm. Diameter: About 3 mm. Texture, upper and lower surface: Smooth, glabrous. Color, upper surface: 196C. Color, lower surface: 185C.

Flower description:

*Flower type and flowering habit.*—Single, rounded, bright red-colored flowers. Freely and continuously flowering; usually about 20 flowers per lateral branch. Flowers positioned just above the foliage; flowers typically face upright to outward, typically parallel to the leaf canopy. Petals not persistent; gynoecium persistent. Flowers not fragrant.

*Flower longevity.*—Flowers last about ten days on the plant.

*Flowering season.*—Year-round under greenhouse conditions. In the garden, plants flower from the spring throughout the summer.

*Flower buds.*—Length: About 1.1 cm. Diameter: About 7 mm. Shape: Ovoid. Color: Between 43C and 45C.

*Flower diameter.*—About 5.4 cm.

*Flower depth* (*excluding spur*).—About 1.8 cm.

*Petals.*—Quantity: Five per flower, imbricate. Length: Banner petals: About 2.4 cm. Lateral and base petals: About 2.6 cm. Width: Banner petal: About 3.5 cm. Lateral and base petals: About 2.9 cm. Shape: Banner petal: Reniform. Lateral and base petals: Broadly obcordate. Apex: Banner petal: Rounded to shallowly retuse. Lateral and base petals: Emarginate. Base, all petals: Attenuate. Margin, all petals: Entire. Texture, all petals, upper and lower surfaces: Smooth, glabrous, satiny. Color: When opening, all petals, upper surface: 44A to 44B. When opening, all petals, lower surface: 44A. Fully opened, all petals, upper surface: 44A. Fully opened, all petals, lower surface: 43A.

*Spur.*—Length: About 3.5 cm. Diameter: About 1.5 cm. Aspect: Curved. Color, immature and mature: 46A.

*Peduncles.*—Length: About 5.5 cm. Diameter: About 2.5 mm. Texture: Smooth, glabrous. Strength: Moderately strong, flexible. Angle: About 45° from vertical. Color: 178B to 178C.

*Reproductive organs.*—Androecium: Stamen number: Five fused at anthers, hooded; filaments free. Anther length: About 2 mm. Anther shape: Obovate. Anther color: 182D. Pollen amount: Scarce. Pollen color: 158D. Gynoecium: Pistil quantity: One per flower. Pistil length: About 1 mm. Stigma color: 158D. Style: Not visible. Ovary: Five-celled. Ovary color: 143A to 143B.

*Seed/fruit.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to tolerate temperatures of about 10° C. to about 35° C.

It is claimed:

1. A new and distinct cultivar of New Guinea *Impatiens* plant named 'Tamar Scarlet Red', as illustrated and described.

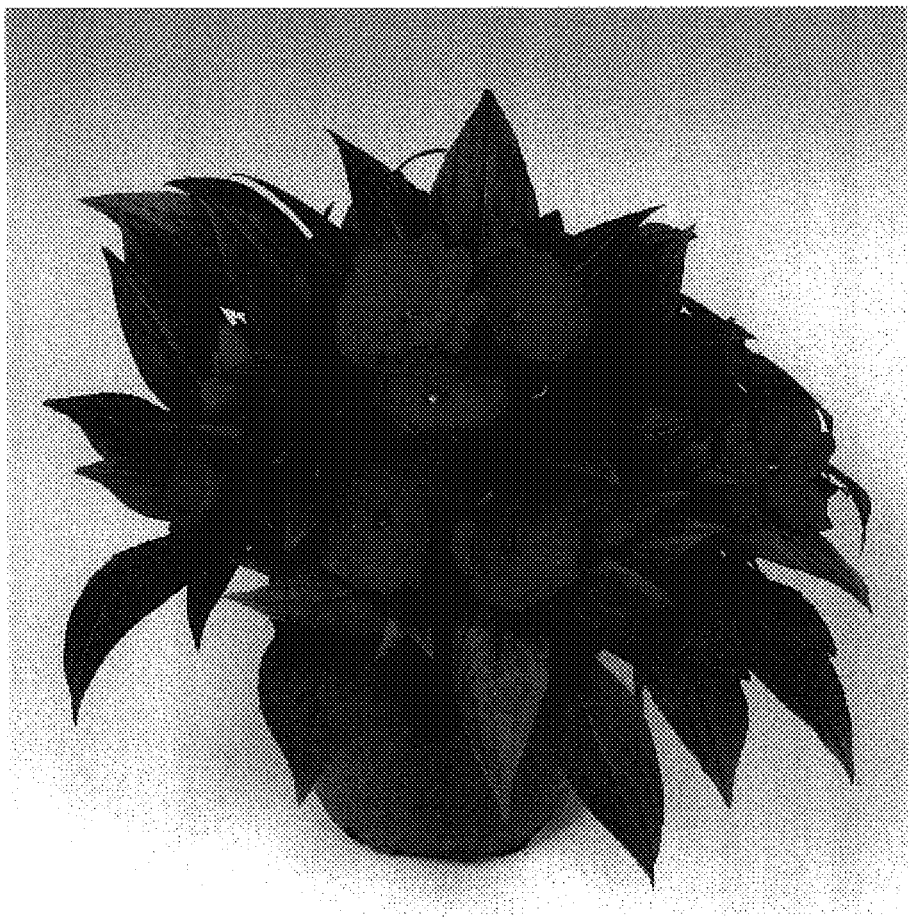

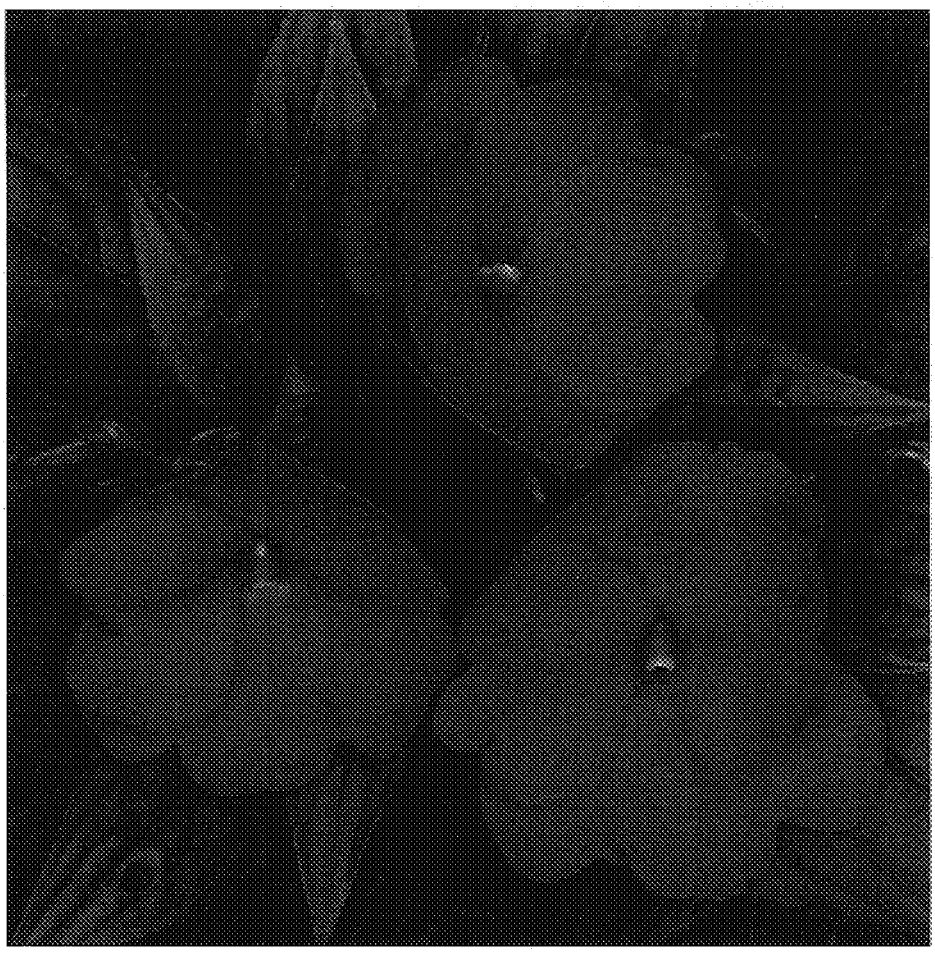

* * * * *